(12) United States Patent
Kidd et al.

(10) Patent No.: US 8,337,848 B2
(45) Date of Patent: Dec. 25, 2012

(54) MONOCLONAL ANTIBODY FOR APP (75) Inventors: Emma Jane Kidd, Cardiff (GB); Janet Eryl Liddell, Sennybridge (GB); Rhian Sara Thomas, Cardiff (GB)

(73) Assignee: University College Cardiff Consultants Limited, Cardiff (GB)

( * ) Notice: Subject to any disclaimer, the term of this patent is extended or adjusted under 35 U.S.C. 154(b) by 115 days.

(21) Appl. No.: 12/739,599

(22) PCT Filed: Oct. 23, 2008

(86) PCT No.: PCT/GB2008/003588
§ 371 (c)(1),
(2), (4) Date: Apr. 27, 2010

(87) PCT Pub. No.: WO2009/053696
PCT Pub. Date: Apr. 30, 2009

(65) Prior Publication Data
US 2010/0239591 A1    Sep. 23, 2010

(30) Foreign Application Priority Data
Oct. 25, 2007   (GB) .................................. 0720912.5

(51) Int. Cl.
A61K 39/395   (2006.01)
C07K 16/18    (2006.01)
C12P 21/08    (2006.01)
C12N 5/07     (2010.01)
C12N 5/20     (2006.01)
C12N 15/13    (2006.01)

(52) U.S. Cl. ............... 424/141.1; 530/388.1; 530/387.9; 435/326; 435/331; 435/320.1; 435/69.6

(58) Field of Classification Search .......................... None
See application file for complete search history.

(56) References Cited

U.S. PATENT DOCUMENTS
2005/0175626 A1* 8/2005 Delacourte et al. ........ 424/185.1
2006/0034855 A1* 2/2006 Solomon .................... 424/185.1
2007/0172484 A1   7/2007 Solomon

FOREIGN PATENT DOCUMENTS
EP    1 717 250    11/2006

OTHER PUBLICATIONS

Alberts B et al. Molecular Biology of the Cell, Third Edition. Garland Publishing, New York, 1994, pp. 1216-1220.*
Kuby J, editor. Immunology, Third Edition. WH Freeman & Co., New York, 1997, pp. 131-134.*
Paul WE, editor. Fundamental Immunology, Third Edition. Raven Press, New York, 1993, pp. 292-295.*
Rudikoff et al. Proc Natl Acad Sci USA, 1982; 79(6):1979-1983.*
Thomas Rhian S et al: "An antibody to the beta-secretase cleavage site on amyloid-beta-protein precursor inhibits amyloid-beta production." Journal of Alzheimer's Disease: JAD Dec. 2006, vol. 10, No. 4, Dec. 2006, pp. 379-390, XP008104271, ISSN: 1387-2877 © 2006—IOS Press and the authors.
Arbel M et al: "Inhibition of amyloid precursor protein processing by beta-secretase through site-directed antibodies" Proceedings of the National Academy of Sciences of USA, National Academy of Science, Washington, DC., US vol. 102, No. 21, May 24, 2005, pp. 7718-7723 XP002500248, ISSN: 0027-8424.
Rakover Idan et al: "Immunotherapy against APP beta-secretase cleavage site improves cognitive function and reduces neuroinflammation in Tg2576 mice without a significant effect on brain abeta levels" Neurodegenerative Diseases, Karger AG, Basel, CH, vol. 4, No. 5, May 25, 2007, pp. 392-402 XP009107314, ISSN: 1660-2854.
Paganetti Paolo et al: "beta-site specific intrabodies to decrease and prevent generation of Alzheimer's A beta peptide" Journal of Cell Biology, vol. 168, No. 6, Mar. 14, 2005, pp. 863-868 XP002520916, ISSN: 0021-9525.

* cited by examiner

Primary Examiner — Elizabeth C Kemmerer
Assistant Examiner — Kimberly A Ballard
(74) Attorney, Agent, or Firm — King & Schickli, PLLC (57) ABSTRACT

The invention relates to a novel peptide, polypeptide or monoclonal antibody for use in the treatment of conditions characterized by elevated levels of β-amyloid (Aβ 39-43 amino acid peptide) in a subject, especially Alzheimer's Disease. The invention particularly relates to an amyloid precursor protein (APP)-binding polypeptide which, when administered outside an APP-expressing cell, reduces the release of Aβ 39-43 by the cell.

16 Claims, 7 Drawing Sheets

MONOCLONAL ANTIBODY FOR APP

This application is the 35 U.S.C. §371 U.S. national stage of International Application No. PCT/GB2008/003588 filed Oct. 23, 2008, which claims the benefit of priority from British Patent Application Ser. No. 0720912.5 filed Oct. 25, 2007. The contents of each application are incorporated by reference herein in their entirety.

FIELD OF THE INVENTION

The invention relates to a polypeptide for use in the treatment of conditions characterised by elevated levels of β-amyloid (Aβ 39-43 amino acid peptide) in a subject, especially Alzheimer's Disease. The invention particularly relates to an Amyloid Precursor Protein (APP)-binding polypeptide which, when administered outside an APP-expressing cell, reduces accumulation or release of Aβ 39-43 by the cell.

BACKGROUND

Alzheimer's Disease (AD) is a progressive neurodegenerative disease characterised by dementia and associated with the elderly. Currently more than 24.3 million people worldwide have dementia, of whom at least half probably have AD. The incidence of AD is likely to increase as the population ages and this will pose a substantial cost to both careers and healthcare systems. Consequently, efforts to prevent or deter the disease will have substantial benefits.

AD has two main characteristic neuropathological features that represent potential therapeutic targets: a massive over-accumulation in the brain of intracellular protein deposits termed neurofibrillary tangles (NFT) and extracellular protein deposits termed amyloid or senile plaques (SP). The main constituent of SP is β-amyloid (Aβ), a 39-43 amino acid peptide that is cleaved from amyloid precursor protein (APP) and is then released from the cell before accumulating to form SP. NFT, consisting of hyperphosphorylated tau protein, are thought to appear after alterations in APP metabolism. An increase in Aβ, levels, especially the 42 amino acid form (Aβ42), leading eventually to excessive deposition and neurotoxicity in the cortex and limbic system in particular, is thought to be crucial for the pathogenesis of AD.

This amyloid hypothesis is one of the dominant theories of the aetiology of AD.

APP, a type-I integral membrane protein, can be processed into fragments by one of two major proteolytic cleavage pathways. The non-amyloidogenic route involves α-secretase which cleaves within the Aβ region to release soluble sAPPα, a 100 kDa secreted isoform that is thought to possess a trophic function in the CNS, and a C-terminal fragment C83 which is cleaved by γ-secretase to produce P3.

APP exists as three major native forms (alternative splice variants) containing 695, 751 and 770 amino acids. Other mutations produce different forms of APP but these are rare. Conserved in each of these isoforms is the β-secretase cleavage site.

The amyloidogenic pathway involves sequential cleavage of APP by β- and γ-secretases. This route first liberates two peptides after cleavage by β-secretase, sAPPβ and C99 (N-terminal and C-terminal fragments, respectively). The latter, C99, is then further processed by γ-secretase to produce Aβ and the APP C-terminal intracellular domain. β-Secretase is an aspartic protease called β-site APP-cleaving enzyme (BACE, sometimes called BACE1). A homologue of BACE1, BACE2, has also been found, predominantly in the pancreas.

Currently, the only licensed treatments available for AD are symptomatic and target glutaminergic and cholinergic systems. Recently, however, the National Institute for Health and Clinical Excellence (NICE) in the U.K. issued guidelines which state that Reminyl™ (galantamine), Aricept™ (donepezil hydrochloride) and Exelon™ (rivastigmine), all acetylcholinesterase inhibitors originally licensed to treat mild to moderate cases of AD, can now only be prescribed on the National Health Service (NHS) for moderate cases of the disease (NICE, 2006). The glutamate receptor antagonist, Ebixa™ (memantine), previously licensed to treat moderately severe to severe cases of AD in the U.K. has been withdrawn from availability via the NHS (NICE, 2006). These drugs can continue to be prescribed for patients already taking them for mild or moderately severe to severe AD before the guidelines were issued (NICE, 2006). As a result of this new guidance, there are no current licensed treatments for mild AD available on the NHS (Alzheimer's Society, 2007).

Potential further treatments currently being researched include antioxidants and cholesterol-lowering drugs. More recent therapeutic research has targeted Aβ accumulation and potential inhibitors of β- and γ-secretase are being developed. However, as γ-secretase also cleaves Notch, which is crucial for cell development and survival, an inhibitor of γ-secretase would need to be selective. β-secretase knockout can have some deleterious effects in mice (Dominguez et al., 2005), suggesting that inhibition of this enzyme might cause problems. It also has other substrates including APP-like proteins (APPLP) 1 and 2, sialyltransferase ST6Gal 1 and P-selectin glycoprotein ligand 1. Furthermore, an inhibitor would have to be specific for BACE1 over BACE2. Finally, it has been suggested that several cysteine proteases have β-secretase-like activity so inhibiting BACE1 alone may not be sufficient to prevent Aβ production.

Other strategies under investigation include research into the reduction of Aβ aggregation, and an understanding of Aβclearance via various systems such as Aβ degrading enzymes and the ubiquitin-proteosome system.

Other workers have targeted Aβ accumulation by interfering with β-secretase activity, and so effectively inhibiting BACE1, by producing antibodies that bind selectively to the β-secretase site of human APP.

Paganetti et al (2005) co-expressed a form of human APP (APP695) and an 'intrabody' consisting of the variable region of an antibody which recognised part of Aβ at a site very close to the β-secretase cleavage site. They observed a stable association between APP and the intrabody which persisted throughout the maturation of APP and resulted in a reduction of intracellular Aβ. Further, not only did this approach protect APP from β-secretase cleavage, it also favoured the alternative cleavage by α-secretase. This resulted in decreased production of the toxic Aβ peptide and the increased production of P3. However, the approach relied on directly transfecting HEK cells with both the intrabody and human APP leading to very high levels of both proteins in their cells. Therapeutically it is very difficult to transfect cells in the brain. Furthermore, even if it were possible to get the DNA into the brain, targeting it to the correct cells and getting the DNA inside the cells would be very difficult. Finally, the intrabody recognises a sequence within the Aβ sequence and may bind to plaques if it leaves the cell. This could trigger an immune response (Citron, 2004) which would be undesirable.

Arbel et al (2005) have also produced antibodies against the β-secretase cleavage site of APP. These workers exploited the cell surface location of APP in order to generate a monoclonal antibody that bound APP at the cell surface prior to being co-internalised into endosomes and thereafter co-existing together through the intracellular trafficking pathways of the cell. In this way a monoclonal antibody specific for the β-secretase cleavage site of APP can be effectively administered and, once bound to its target site, provides sustained inhibition of BACE cleavage of APP. The β-secretase cleavage site resides between amino acids 663 and 671 of APP and comprises the sequence ISEVKMDA (SEQ ID NO: 1) (Arbel et al. 2005). To improve the immunogenicity of their peptide and reduce tolerance to self-antigens, Arbel et al prepared a multiple antigenic peptide (MAP) expressing eight copies of the APP β-secretase cleavage site containing half the Swedish mutation (ISEVKLDA; SEQ ID NO: 2). Using this MAP a monoclonal antibody, designated BBS 1, was identified. Following internalisation into Chinese hamster ovary cells overexpressing human APP, BBS 1 reduced extracellular and intracellular Aβ levels. In addition, the same group injected APP mutant mice with their antibody and showed an improvement in cognition but no effect on Aβ levels (Rakover et al., 2007). Taken together with our own results, these studies suggest that steric hindrance may be a viable method of reducing amyloid production in vivo.

Our own work (Thomas et al 2006) has also shown that it is possible to produce monoclonal antibodies specific for the β-secretase site of APP, in particular monoclonal antibody 2B12. Thus, via steric hindrance, we can inhibit cleavage of APP and so reduce downstream production of Aβ. As with Arbel et al we believe that our monoclonal antibody 2B12 can enter cells by binding to APP when it is at the cell surface and then being internalised when bound to its antigenic protein. However, with 2B12 we were unable to inhibit more than 45% of Aβ40 production and we therefore concluded that perhaps not all APP is trafficked to the cell surface or the less than desirable inhibition was a function of the affinity of the antibody.

However, our subsequent experiments have revealed that it is possible to achieve better results by using a surprisingly active monoclonal antibody that has the ability to bind to APP more efficiently and thus can more effectively inhibit the β-secretase-mediated cleavage of APP. We have called this particularly effective monoclonal antibody 2B3-E10-A8-B10-F10-H3 (2B3).

Notably, although our invention has been described having regard to Alzheimer's Disease it has use in the treatment of conditions characterised by elevated levels of β-amyloid (Aβ 39-43 amino acid peptide) in a subject.

SUMMARY OF THE INVENTION

According to a first aspect of the invention there is provided an Amyloid Precursor Protein (APP)-binding polypeptide which, when administered outside an APP-expressing cell, reduces the accumulation or the release of β-amyloid (Aβ 39-43).

Reference herein to a polypeptide includes reference to a polypeptide regardless of its length and so also includes reference to a protein or a peptide.

This APP-binding polypeptide is, ideally, a monoclonal antibody or a fragment of a monoclonal antibody and, in the latter instance, more particularly, the whole or a part of the variable domain such as the whole variable domain or an antigen-binding fragment thereof.

In a preferred aspect of the invention the APP-binding polypeptide binds to the whole or a part of the β-secretase cleavage site of APP (ISEVKMDA; SEQ ID NO: 1) and more preferably still is generated using the antigenic peptide EEISEVKMDAEFRHD (SEQ ID NO: 3) when, ideally, said peptide is conjugated to a multi-antigenic peptide.

Multi-antigenic peptides are well known to those skilled in the art. They comprise carriers having a branched poly-lysine core. This core forms a backbone to which, via the α- and ε-amino functional groups of lysine, multiple peptide chains can be attached. Depending on the number of lysine tiers (2, 4, 8, etc.), different numbers of peptide branches can be attached. In our case 8 identical peptides, as described above, were attached to the core. This generated a high ratio of peptide to core. The poly-lysine core is generally considered to be of low antigenicity, however, when selecting antibodies, we were careful to ensure that only those that recognised the antigenic peptide were chosen. The MAPs used in the studies described herein were generated by Severn Biotech Ltd based in Kidderminster, UK.

According to a further aspect of the invention there is provided a monoclonal antibody that binds to amyloid precursor protein (APP), when administered outside an APP-expressing cell, to reduce the release or accumulation of β-amyloid (Aβ 39-43) protein by said cell wherein the monoclonal antibody is 2B3-E10-A8-B10-F10-H3(2B3).

Notably, this is an IgG1 class antibody.

The monoclonal antibody of the invention has been deposited with the European Collection of Cell Cultures (ECACC) under accession numbers 07100204 (2.10.07) and 08101701 (17.10.08).

In a preferred aspect of the invention the antibody selectively binds to a thrombin cleavage fragment of APP, ideally this fragment has a MW of 56 KDa.

Reference herein to a thrombin cleavage fragment includes reference to the fragment described in Chong et al (1994).

In a preferred embodiment of either aspect of the invention the binding of the polypeptide or monoclonal antibody to the APP protein results in a reduction in β-amyloid (Aβ 39-43) such that there is a greater than 45% inhibition of β-amyloid (Aβ 39-43) accumulation or release.

Alternatively, or additionally, in a preferred embodiment of either aspect of the invention the half-maximal binding of the polypeptide or monoclonal antibody to the APP protein is less than 2.96 ug/ml.

In a preferred embodiment of either aspect of the invention the APP-expressing cell is a mammalian cell or a mammalian cell line and more specifically a human cell or a human cell line.

According to a further aspect of the invention there is provided a method for the treatment of an individual suffering from, or suspected to be suffering from, Alzheimer's Disease or an aetiologically related disease that is characterised by the production of β-amyloid (Aβ 39-43) wherein an effective amount of polypeptide or monoclonal antibody (2B3) of the invention is administered to an individual to be treated.

In a preferred method of the invention the polypeptide or monoclonal antibody, 2B3, is administered outside an APP-expressing cell of an individual to be treated. Most preferably, an effective amount of polypeptide or monoclonal antibody is administered, or injected, intravenously, subcutaneously or intramuscularly. Less typically the polypeptide or monoclonal antibody is administered, or injected into the cerebral spinal fluid and, more particularly, the polypeptide or monoclonal antibody is administered or injected at a site to be treated and therefore may be administered or injected intracranially into a target region of a mammalian brain and ideally a human brain. Alternatively the polypeptide or monoclonal antibody is formulated for oral or sublingual administration. Alternatively still, the polypeptide or monoclonal antibody is formulated for nasal administration or for inhalation administration. Alternatively, again, the polypeptide or monoclonal antibody is provided as a depot injection or implant.

According to a further aspect of the invention there is provided a pharmaceutical composition comprising either an effective amount of APP-binding polypeptide or the monoclonal antibody of the invention.

In a preferred embodiment of this aspect of the invention the pharmaceutical composition reduces the accumulation or release of β-amyloid (Aβ 39-43) protein from an APP-expressing cell or cell line by greater than 45% of said cell's normal production.

In a preferred embodiment of the invention said pharmaceutical composition comprises a pharmaceutically acceptable adjuvant, carrier or vehicle.

In a further aspect of the invention there is provided an APP-binding protein characterised by its selective binding to an APP thrombin cleavage fragment.

According to a further aspect of the invention there is provided a cell or cell line which secretes the polypeptide or monoclonal antibody, 2B3, of the invention.

According to a yet further aspect of the invention there is provided a vector including a nucleic acid molecule encoding the APP-binding polypeptide or the monoclonal antibody of the invention.

In this preferred aspect of the invention the vector is adapted for transforming or transfecting a selected host cell whereby, once incorporated into the host cell, the vector is suitably engineered or integrated for the purpose of ensuring that the host cell produces the APP-binding polypeptide or the monoclonal antibody of the invention.

Those skilled in the art will be familiar with the nature of the adaptations that need to be secured in order to ensure that a host cell secretes a protein encoded by the nucleic acid sequence of the vector.

BRIEF DESCRIPTION OF THE DRAWINGS

An embodiment of the invention will now be described by example only with reference to the following Figures wherein.

DETAILED DESCRIPTION OF THE INVENTION

Materials and Methods
Immunisation Procedures

Monoclonal antibodies were raised against an immunogenic peptide (EEISEVKMDAEFRHD; SEQ ID NO: 3), termed Ka, which represented the amino acid sequence spanning the β-secretase cleavage site in human APP. The peptide was synthesised using a poly-lysine, multiple antigenic peptide (MAP) core and then used to immunise female Balb/c mice (20-25 g). All experiments on mice were performed in accordance with the Animals (Scientific Procedures) Act 1986 administered by the U.K. Government Home Office and with ethical approval from Cardiff University. Mice were immunized and hybridomas were generated by standard methods as first developed by Kohler and Milstein (1975) and detailed elsewhere, including Liddell and Cryer (1991). The hybridoma supernatants were screened for high-affinity MAbs by indirect ELISA using the immunising peptide, prior to more complete cross-reactivity screenings. The 2B3 and 2B 12 clones were chosen for further screening based on preliminary experiments.

Cell Culture

A human cell line, astrocytoma MOG-G-UVW (MOG), which constitutively expresses APP, was used to investigate the characteristics of 2B3 and 2B12. The cells were used as a source of APP and to characterise the binding properties of 2B3 and 2B12. They were also used as a model system to investigate whether 2B3 and 2B12 could reduce Aβ40 levels and for cell viability studies. MOG were grown in a 1:1 solution of Ham's F10 and Dulbecco's Modified Eagle's Medium supplemented with 10% Foetal Bovine Serum (FBS) (Perbio Science U.K. LTD, Cramlington, U.K.) and 2 mM glutamine. Cell lines were incubated at 37° C. in 5% $CO_2$ in air.

Antibody Processing

The 2B3 and 2B12 antibodies were concentrated from culture medium using Amicon Centriplus YM-100 filters (Millipore, Billerica, Mass., USA) with a nominal molecular weight cut off of 100 kDa and the isotype determined using the Isostrip mouse monoclonal antibody isotyping kit (Serotec, Oxford, U.K.).

Detection of 2B3 and 2B12 Binding to APP by Western Blotting

Western Blotting was performed using standard methods (Kidd et al 1998). The samples and molecular weight marker (Precision Plus Protein Standards marker, Bio-Rad Laboratories, Hercules, Calif.) were loaded onto 10% polyacrylamide gels and separated by sodium dodecyl sulphate-polyacrylamide gel electrophoresis (SDS-PAGE) in running buffer (25 mM Tris base, 190 mM glycine, 0.05% SDS, pH 8.3). The separated proteins were then blotted on to 0.2 μm nitrocellulose membranes (Amersham Biosciences, Little Chalfont, UK), washed in Tris-buffered saline with Tween 20 (TBST, 2 mM Tris, 15 mM NaCl, 0.1% Tween-20, pH 7.5) and blocked for 1 hour, at room temperature (RT), in TBST supplemented with 5% w/v fat-free dried milk (Blotto). Blots were then incubated with the relevant antibody in 1% Blotto at 4° C. overnight. Membranes were washed five times in TBST and incubated with the relevant horseradish peroxidise (HRP)-conjugated secondary antibody (1:20,000, Vector Laboratories, Burlingame, Calif.) for 1 hour at RT. The membranes were washed as above in TBST, the bands visualised using enhanced chemiluminescent detection (Super Signal®, West Dura, Perbio Science U.K.) and exposed to high performance chemiluminescent X-ray film (Amersham Biosciences).

Binding of 2B3 and 2B12 to APP

We used a competition assay in conjunction with a sandwich ELISA which recognised an epitope in the region of the C-terminus of APP (APP DuoSet, R & D Systems, Abingdon, U.K.). Lysates were prepared from MOG cells using lysis buffer (50 mM Tris, 5 mM EDTA, 150 mM NaCl, 1% Triton, 0.4 mM $NaVO_4$, 50 mM NaF, 1 mM PMSF, 20 μM phenylarsine oxide, 10 mM sodium molybdate, 10 μg/ml leupeptin, 10 μg/ml aprotinin) and then concentrated through Amicon Centriplus YM-100 centrifugal filters with a nominal molecular weight cut-off of 100 kDa. Recovered APP was quantified using a sandwich ELISA by comparing values with standard recombinant human βPP from the APP DuoSet. The ELISA followed the manufacturer's guidelines. Briefly, the capture antibody was used at 4 μg/ml in phosphate-buffered saline (137 mM NaCl, 1.5 mM $KH_2PO_4$, 8 mM $Na_2HPO_4.12H_2O$, 2.5 mM KCl, pH 7.4) (PBS) to coat 96-well microplates (Greiner Bio-One, Stonehouse, U.K.) and incubated overnight at room temperature (RT). Plates were blocked with 1% bovine serum albumin (BSA) and 5% sucrose in PBS for a minimum of 30 minutes. Samples and standards were prepared in 1% BSA in PBS and incubated on the plate for 2 hours. A six point standard curve was prepared with a highest concentration of 20 ng/mL. Biotinylated detection antibody, 300 ng/ml in 1% BSA in PBS, was incubated for 1.5 hours and detected using streptavidin-HRP, diluted 1:200 in PBS with 0.05% Tween 20 (PBST) for 20 minutes, followed by the enzyme substrate, o-phenylenediamine (OPD), in 0.1M citrate-phosphate buffer, pH 5.0, incubated for 20 minutes. The reaction was stopped with 2.5M $H_2SO_4$ and the absorbance determined, at 492 nm. All incubations were performed at room temperature (RT), unless otherwise stated and wells were aspirated and washed four times with PBST between each stage. The competition assay for APP followed the same protocol except for the following modifications. MOG cell lysate was used to provide APP at a concentration of 30 ng/ml. Prior to incubating with the detection antibody, the samples were incubated with 2B3, B12 or an irrelevant mouse IgG antibody (Perbio Science) from 1 to 20 μg/ml for 1 hour. Binding of these antibodies was then inferred by a decrease in binding of the detection antibody compared to the PBST control alone.

Affinity Ranking of 2B3 and 2B12 Binding

Affinity ranking of the two antibodies was accomplished by comparing their binding properties to a peptide, Kb, which spans the β-secretase cleavage site on APP, in an indirect ELISA. This peptide represents a 15 amino acid sequence (SEVKMDAEFRHDSGY; SEQ ID NO: 4), slightly further into the Aβ region of APP than Ka, the immunising peptide. Kb was adsorbed to a 96 well microtitre plate at a concentration of 10 ug/ml in carbonate/bicarbonate buffer (15 mM $Na_2CO_3$, 35 mM $NaHCO_3$, pH9.8) overnight at 4° C. Plates were then blocked with 1% (w/v) non-fat milk powder in PBST for 1 hour. 2B3 or 2B 12 were incubated for 2 hours at concentrations ranging from 0.00001 to 30 μg/ml and detected with a secondary anti-mouse antibody conjugated to HRP, 1:2500 (Pierce) for 1 hour, followed by OPD and detection as above. All results were expressed as a proportion of a standard antibody (6E10, Chemicon, Chandlers Ford, U.K.) at 0.05 ug/ml. Curve fitting was performed using GraphPad Prism® version 4.

Persistence of 2B3 and 2B12 Binding in a Range of pH Buffers

The binding persistence of 2B3 and 2B12 to Kb was investigated at a range of pH values using an indirect ELISA. Methods followed those detailed above with the following modifications. Kb was adsorbed and blocked as above. 2B3 and 2B12 (5 μg/ml) were incubated with Kb for 1 hour in PEST pH 7.4 and the antibody solution was aspirated. The immunocomplex was then incubated for up to a further hour in PBST at either pH 7.4, 6, 5 or 4 for 0, 15, 30 or 60 minutes. Binding of both antibodies was detected as above and all results were expressed as a proportion of a standard antibody (6E10) at 0.05 μg/ml. PBS was adjusted to the correct pH with $H_3PO_4$.

Binding of 2B3 and 2B12 to sAPPα and sAPPβ

The epitopes of 2B3 and 2B12 on APP were investigated by comparing the relative binding profiles of the antibodies to cleavage products of APP in an indirect ELISA. Methods 20, followed those detailed above with the following modifications. Recombinant sAPPα and sAPPβ (Sigma) were adsorbed to a 96 well microtitre plate at a concentration of 5 ug/ml (in carbonate/bicarbonate buffer) overnight at 4° C. Plates were blocked with 1% non-fat milk powder for 1 hour and 2B3 and 2B12 subsequently incubated at 1 ug/ml for 2 hours. Binding of both antibodies was detected as above and binding to sAPPβ was expressed as a percentage of the binding of the respective antibody to sAPPα.

Effect of 2B3 and 2B12 on MOG Cell Viability

Viability studies were performed on MOG cells after incubation with 2B3 or 2B12 using the MTS (3-(4,5-dimethylthiazol-2-yl)-5-(3-carboxymethoxyphenyl)-2-(4-sulfophenyl)-2H-tetrazolium inner salt) assay (CellTiter 96® Aqueous One Solution Cell Proliferation Assay, Promega). MOG cells were added to 96-well cluster plates at a concentration of 2000 per well in 100 µl, allowed to adhere overnight and then incubated with 100 µl of either 2B3, 2B12 (10 ug/ml) or media control for 48 hours. 20 µl CellTiter 96® AQueous One Solution Reagent was added directly to the culture wells and incubated in the dark for 1.5 hours. The resulting formazan product was quantified by measuring absorbance at 490 nm and results were expressed as a percentage of media control values.

Effects of 2B3 and 2B12 on Aβ40 Levels

All experiments were performed in 24 well cluster plates. $1.08 \times 10^4$ MOG cells were plated per well. All samples were done in triplicate on each plate. Cells were allowed to attach overnight then incubated with control media, 2B3, 2B12, an anti-N-terminal APP antibody (Millipore, Watford, U.K.) or the irrelevant mouse IgG (all at 10 µg/ml) in relevant culture media for 2 days at 37° C. For subsequent analysis of Aβ40, 450 µl of media were collected from each well and subjected to combined immunoprecipitation and ELISA. Media was first immunoprecipitated with 1:2,000 BAM401S (Autogen Bioclear, Calne, U.K, specific to the C-terminus of human Aβ40, overnight at 4° C. Samples were then incubated with Protein A (Santa Cruz Biotechnology, Santa Cruz, Calif., USA) for 2 hours and then washed with CHAPS buffer (150 mM NaCl, 50 mM Tris, 1 mM EDTA, 10 mM CHAPS) and centrifuged at 3275 g, repeated 3 times. This was followed by a final wash in PBS. Samples were then boiled at 95° C. for 5 minutes to dissociate the Protein A before being centrifuged for 1 minute at 3275 g. The supernatant was subsequently removed and tested in an ELISA for Aβ40 following the methods above, except for the following. The ELISA employed the N-terminal Aβ MAb 6E10 (Chemicon), as the capture antibody and affinity-purified BAM401AP (Autogen Bioclear), specific to the C-terminus of human Aβ40, as the detection antibody. 6E10, 5 µg/ml in carbonate/bicarbonate buffer, was incubated overnight at 4° C. Plates were then blocked with 0.1% milk powder in PBS for 1 hour. Samples and standards were added to the plates and incubated for 1.5 hours followed by the detection antibody, 0.45 µg/ml in PBST for 1.5 hours. The plates were then blocked for 30 minutes and a secondary anti-rabbit antibody conjugated to HRP, 1:2500 (Vector Laboratories), was incubated for 1 hour. Binding was detected with OPD as above. This resulted in an ELISA with a lower limit of sensitivity of approximately 0.1 ng/ml giving good differentiation within the range of Aβ40 immunoprecipitated from the cell lines. The concentration of Aβ40 in samples from the cells was calculated from an Aβ40 standard curve (0-12.5 ng/ml) run on the same plates and generated in GraphPad Prism and normalised to the total cell protein content. Aβ40 concentrations were then expressed as a percentage of the relevant control values.

Statistical Analyses

The competition assay data were analysed by two methods. Differences from media controls at 100% were analysed with Student's t-tests while differences between 2B3 and 2B12 were analysed using ANOVA followed by Bonferroni post-hoc tests. Affinity ranking of 2B3 and 2B12 was performed using Graphpad Prism® 4. Log antibody concentration was plotted against % absorbance and a sigmoidal dose-response curve fitted to the data. Curve parameters were compared using the F-test. Differences between 2B3 and 2B12 at each concentration were compared using a Student's t-test. The persistence in binding of the two antibodies, at a range of pH values, was investigated separately, using GLM univariate analysis, with absorbance as the dependent variable and pH and time as factors. This was followed by Bonferroni post-hoc tests. Antibody (either 2B3 or 2B12) binding to sAPPβ was expressed as a % of binding to sAPPα(100%). This value was compared to 100% with a Student's t-test. The % change in binding to the two fragments for each antibody was also compared using a Student's t-test. The absorbance obtained at 490 nm in the MTS assay, after incubation with either 2B3 or 2B12, was expressed as a % of media control (100%) and this value was again compared to 100% with a Student's t-test. The data generated in the ELISA to measure Aβ40 levels were analysed using a Student's t-test to determine if Aβ concentrations were significantly lower than media controls (100%) or if there was a significant difference between 2B3 and 2B12. Unless specified, data analyses were performed using SPSS 12. All comparisons were made at the two-tailed significance level.

Results

Figure 1:
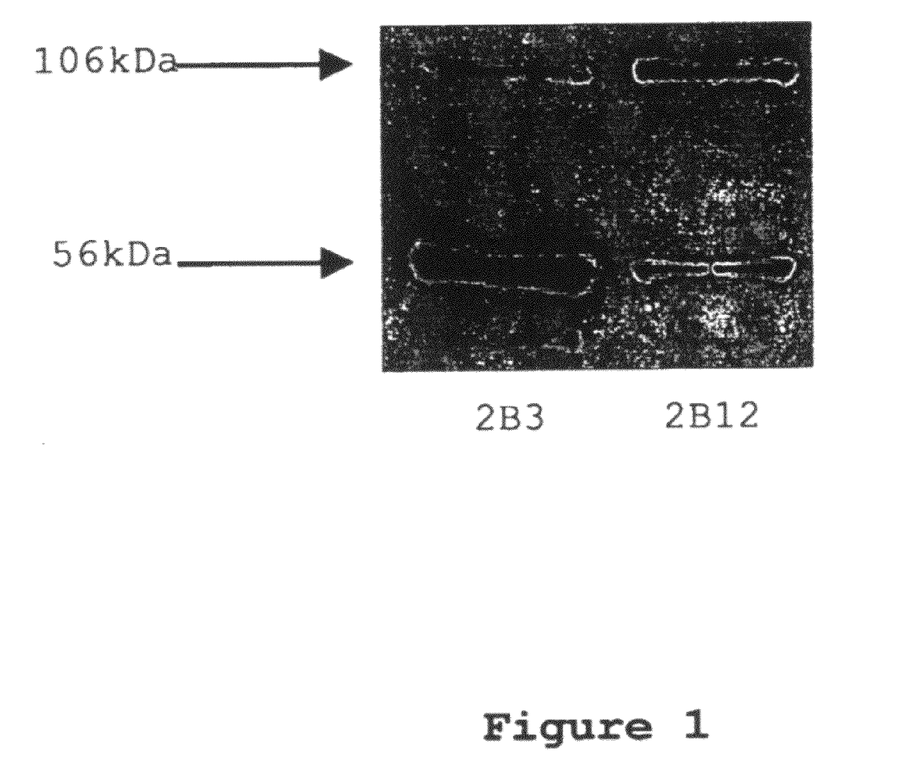
FIG. 1 is representative of the binding of 2B3, and as a comparison, 2B12, to 50 μg lysate from MOG-G-UVW (MOG) cells using Western Blotting, both antibodies were tested at 2 μg/ml. Binding to full length APP (106 KDa) and to a thrombin cleavage fragment (56 KDa) of APP was detected for both antibodies. In addition, 2B3 detected other bands which were not seen with 2B12 even after long exposure. n=3.

2B3 was generated with the same peptide, Ka (EEISEVKMDAEFRHD; SEQ ID NO: 3) conjugated to a MAP core, used to make 2B12. However, the two antibodies are different as 2B12 is of the IgG2b class while 2B3 is an IgG1. Importantly, the two antibodies also bind to different epitopes as the pattern of binding revealed by Western blotting for APP from cell lysates of MOG cells which constitutively express APP is different (FIG. 1). Both antibodies recognise APP (106 kDa band) but the binding of 2B12 to this band is stronger than that to the 56 kDa band thought to be the thrombin cleavage product. However, the reverse is seen with 2B3 which binds more strongly to the 56 kDa fragment than to full-length APP. Furthermore, additional bands, probably other fragments of APP, were detected with 2B3 but were not seen with 2B12. Therefore the antibodies are clearly not the same.

Figure 2:
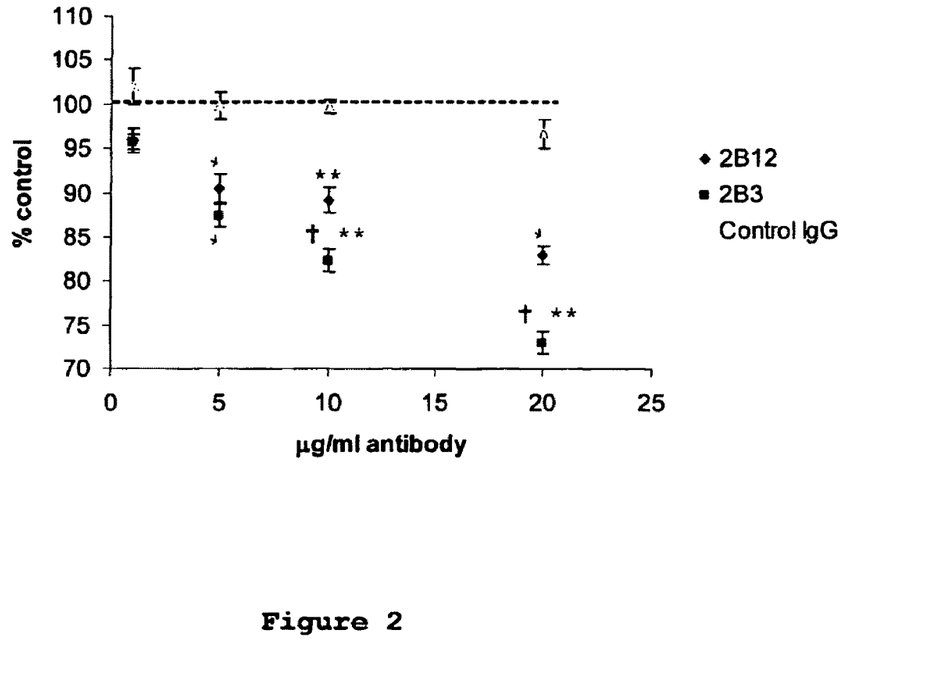
FIG. 2 shows a competition sandwich ELISA for APP from concentrated MOG cell lysate using anti-APP antibodies from the APP DuoSet (capture and detection antibodies at 4 μg/ml and 300 ng/ml, respectively). Prior to incubation with the detection antibody, ELISA plates were coated with a range of concentrations of 2B12, 2B3 or an irrelevant mouse IgG antibody. Controls of media were also included and data are expressed as mean % of control absorbance (+/−SEM). Differences from media controls at 100% were analysed with two-tailed Student's t-tests; *p<0.01, **p<0.001. Differences between 2B3 and 2B12 were analysed using ANOVA followed by Bonferroni post-hoc tests; † p<0.05. The irrelevant IgG had no effect on the ELISA. n=4.

2B3 binds more effectively to APP than 2B12 as demonstrated by a competition assay to detect binding to APP (FIG. 2). A commercial ELISA kit to measure binding to APP was used to quantify the binding of both antibodies. Here, one antibody from the kit was used to capture APP from MOG cell lysate and media or 1-20 µg/ml of 2B12, 2B3 or an irrelevant mouse IgG was added to bind to a different epitope on APP.

Finally, the second antibody from the kit was used which binds to a third epitope on APP. Any reduction in the binding of the second antibody seen with 2B12, 2B3 or the irrelevant mouse IgG was expressed as a percentage of the media control.

FIG. 2 clearly shows that, even at a very high concentration of the irrelevant IgG (20 µg/ml), the binding of the second commercial antibody was only reduced non-significantly by 3.3%, probably due to non-specific binding arising from the high concentration of protein present. At and 20 µg/ml 2B12 significantly reduced the binding of the second commercial antibody by 10.9 and 17.1%, respectively, similar to the levels we had seen previously (Thomas et al., 2006). However, at 10 and 20 µg/ml 2B3 significantly reduced the binding of the second commercial antibody by 17.7% and 27.1%, respectively. These were significantly greater reductions than those seen with 2B12. Therefore we can conclude that 2B3 binds significantly more efficiently to APP than 2B12. This experiment also provides further confirmation that the two antibodies are not the same and bind to different epitopes.

Figure 3:
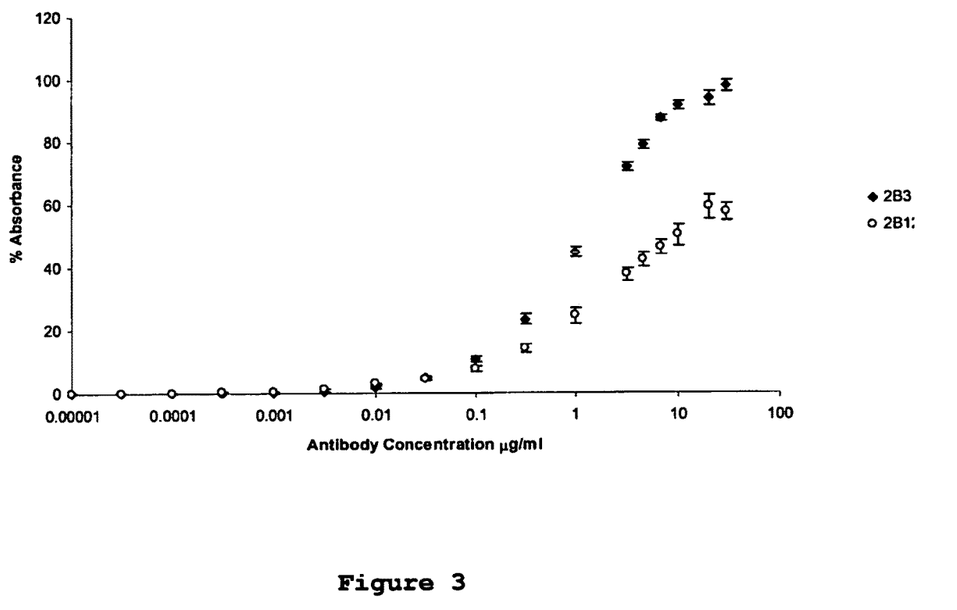
FIG. 3 shows an ELISA to determine the half-maximal binding of 2B3 and 2B12 to the peptide Kb which spans the β-secretase cleavage site. Data are expressed as a proportion of standard antibody (6E10) at 0.05 μg/ml (+/−SEM). Log antibody concentration was plotted against % absorbance and a sigmoidal dose-response curve fitted to the data. Curve parameters were compared using the F-test. Differences between 2B3 and 2B12 at each concentration were compared using a Student's t-test; * p<0.05. n=3-4.

The comparison of the half-maximal binding of 2B3 and 2B12 to the peptide Kb (SEVKMDAEFRHDSGY; SEQ ID NO: 4), which spans the 13-secretase cleavage site, confirmed these results. The half-maximal concentration for binding of 2B3 to Kb, 1.279 µg/ml (95% confidence interval (CI) 1.153 to 1.418), was significantly lower than that of 2B12, 2.963 µg/ml (CI-1.696 to 5.177) ($p<0.0001$). In addition, the entire curve for 2B3 binding to Kb was significantly different to that for 2B12 ($p<0.0001$) and the binding of 2B3 to Kb was significantly higher than 2B12 at all concentrations greater than 0.1 µg/ml ($p<0.05$, FIG. 3). These data further support our contention that the two antibodies are not the same.

Figure 4:
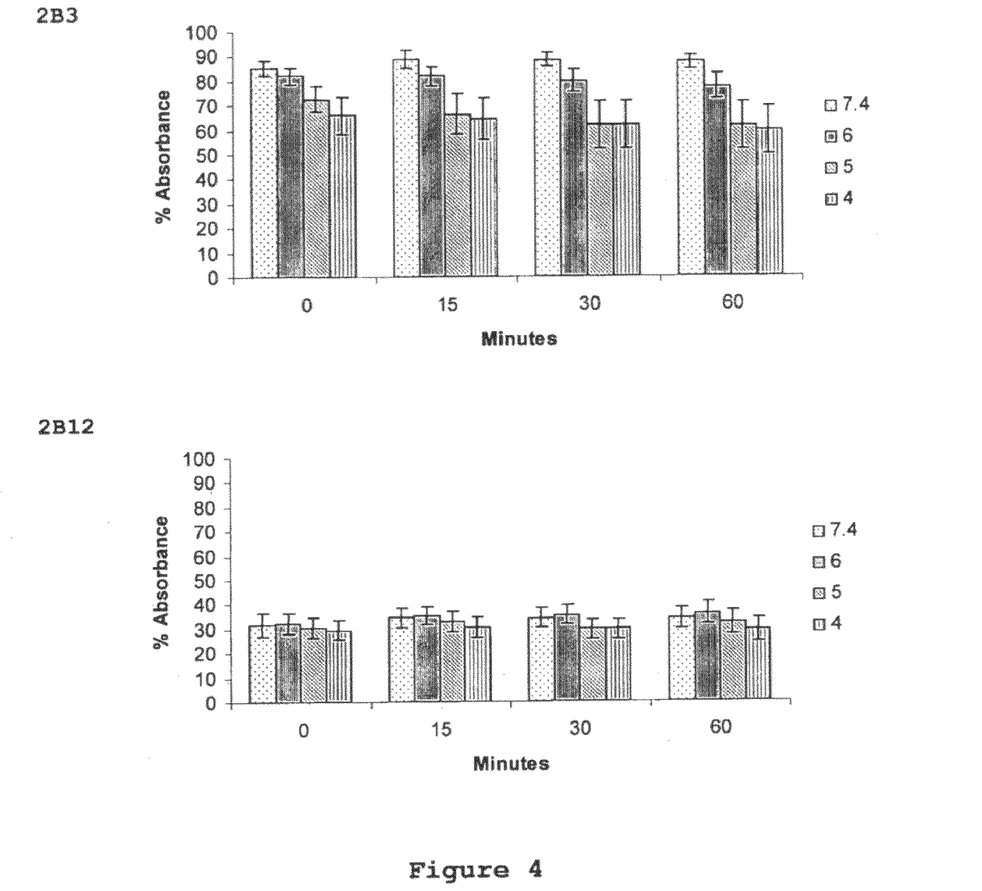
FIG. 4 shows the effect, of different pH values on persistence of binding of 2B3 and 2B12 to Kb. ELISA plates were coated with 10 μg/ml Kb and then incubated with 2B12 or 2B3 (5 μg/ml) for 1 hour at pH7.4. The antibodies were then incubated for up to a further hour in different solutions at pH 7.4, 6, 5 or 4. The persistence in binding of the two antibodies, at a range of pH values, was investigated separately, using GLM univariate analysis, with absorbance as the dependent variable and pH and time as factors. This was followed by Bonferroni post-hoc tests. n=3.4.

2B3 and 2B12 will bind to APP outside the cell at pH 7.4 but, once internalised into endosomes/lysosomes, they will be subjected to a much lower pH environment around pH 4.5. Therefore we tested the persistence of binding of a single concentration (5 µg/ml) of 2B3 and 2B12 to Kb at different pH values. The antibodies were bound to the peptide at physiological pH 7.4 and then incubated for different periods of time at pH 4, 5, 6 or 7.4. We showed that the binding of 2B3 to Kb was significantly affected by pH with a reduction in binding compared to pH 6 and pH 7.4 seen with pH 4 ($p<0.01$, $p<0.0001$, respectively) and 5 ($p<0.05$, $p<0.0001$, respectively) (FIG. 4). However, the time of incubation at different pH values did not significantly affect the binding. The binding of 2B12 to Kb was not significantly affected by pH or time of incubation (FIG. 4). These data are important as they show that, although 2B3 binding was reduced at lower pH values, it still had higher binding than 2B12 at all pH values and time points. Furthermore the lack of effect of time suggests that the antibodies will continue to work to prevent β-secretase access inside the cell for a biologically relevant period of time. Finally, these findings support earlier evidence that 2B3 and 2B12 are different antibodies.

Figure 5:
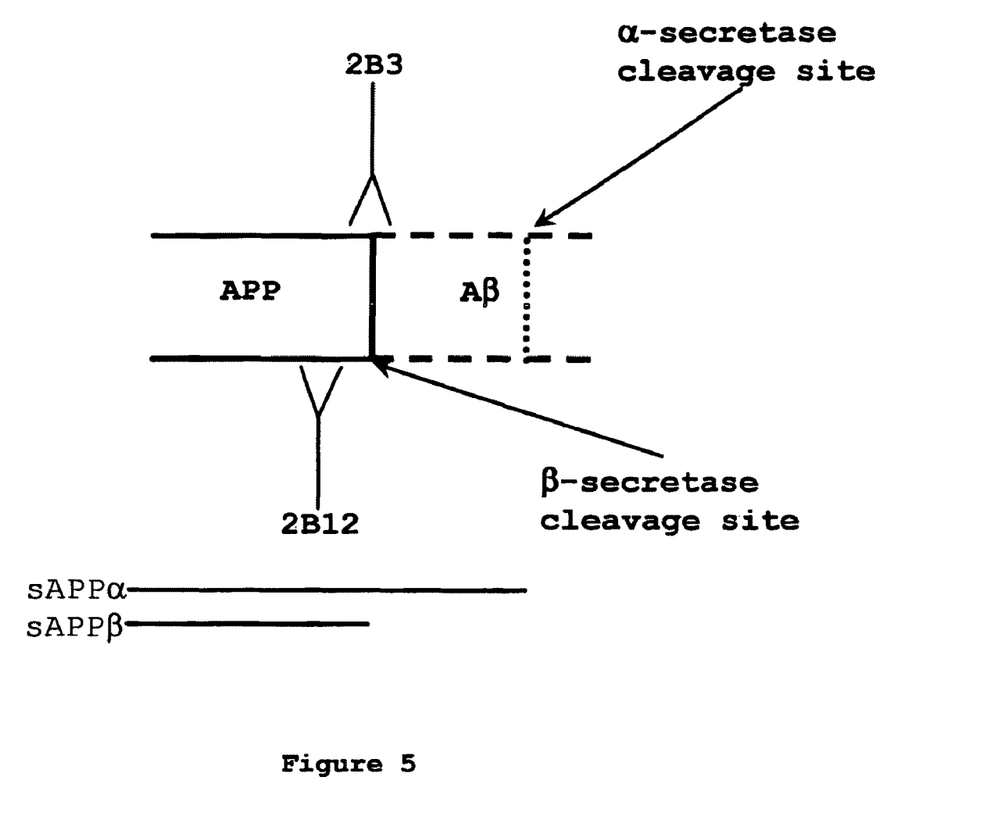
FIG. 5 compares the likely binding sites of 2B3 and 2B12 to fragments of APP and Aβ. Only the parts of APP and Aβ around the enzyme cleavage sites are shown. 2B3 binds to sAPPβ less well than to sAPPα suggesting that it binds across the β-secretase cleavage site. 2B12 recognises sAPPα and sAPPβ to a similar extent so is likely to bind upstream of the β-secretase cleavage site in the region common to sAPPα and sAPPβ.

Additional evidence to support our contention that 2B3 and 2B12 are different antibodies with different epitopes comes from studies looking at the binding of these two antibodies to sAPPα and sAPPβ, produced from APP by the cleavage of α- and β-secretases, respectively. The % of antibody bound to sAPPβ compared to sAPPα was 76.2±1.7% for 2B3 and 105.6±2.1% for 2B12. The % bound for 2B3 was both significantly different from 100% ($p<0.01$) and from 2B12 ($p<0.001$) while the % bound for 2B12 was not different from 100%. These data show that 2B3 recognises sAPPα better than sAPPβ while 2B12 recognises both APP fragments to a similar extent. This is probably due to differences in binding sites with the likely epitope of 2B3 being more in Aβ than that for 2B12 (FIG. 5), although importantly neither antibody binds to Aβ per se.

Figure 6:
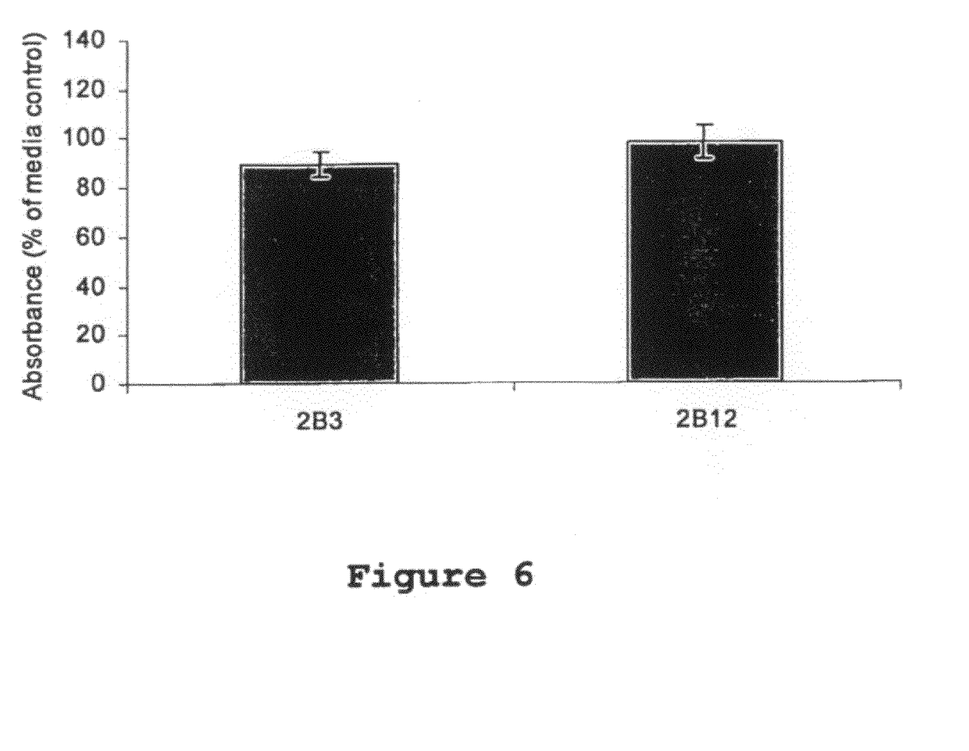
FIG. 6 shows the effect of 2B3 and 2B12 on cell viability measured using an MTS assay. MOG cells were incubated with 2B3, 2B12 (10 μg/ml) or media control for 48 h. Cell-Titer 96® AQueous One Solution Reagent was added directly to the culture wells and incubated in the dark for 1.5 hours. The resulting formazan product was quantified at 490 nm and results expressed as % of media control values. Differences from media controls at 100% were analysed with two-tailed Student's t-tests. n=3-6.

We have previously show that 2B12 was not toxic to cells in culture (Thomas et al., 2006) and have now extended this data to compare the effect of 2B3 and 2B12 on the growth of MOG cells. Cells were incubated with either antibody at 10 µg/ml for 2 days (same time course as for the inhibition of Aβ production) and the numbers of viable cells were then measured using an MTS assay. Neither antibody had any significant effect compared to the media control on the number of viable cells measured after 48 hours (FIG. 6). These data demonstrate that 2B3 is not toxic to cells in culture and that the reductions seen in Aβ40 levels are due to another mechanism besides cell death.

Figure 7:
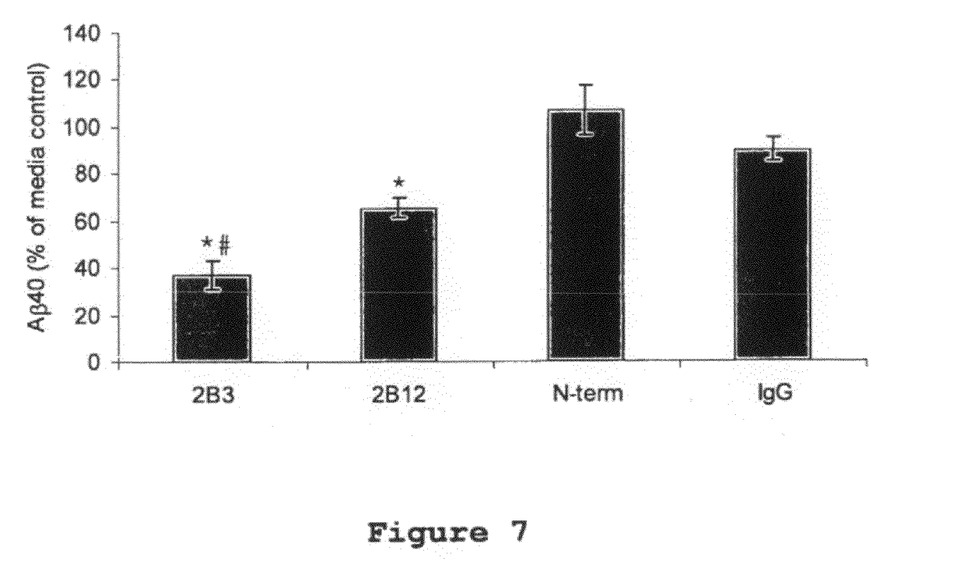
FIG. 7 shows the effect of 2B12, 2B3, an anti-N-terminal APP antibody or an irrelevant mouse IgG on Aβ40 levels in MOG cells. Data are expressed as mean (+/−SEM) % of control (media only) Aβ40 levels as detected in a sandwich ELISA and corrected for total cell protein content. Cells were incubated with 10 μg/ml 2B12, 2B3, anti-N-terminal APP antibody or the irrelevant IgG for 2 days. Differences from media controls at 100% and between 2B3 and 2B12 were analysed with two-tailed Student's t-tests. 2B12 significantly reduced Aβ40 levels from control, * p<0.05. 2B3 significantly reduced Aβ40 levels from control, p<0.001, and 2B12, † p<0.02. The anti-N-terminal APP antibody and the irrelevant IgG had no effect on Aβ40 levels. n=3-6.

Having demonstrated that 2B3 bound more efficiently to APP than 2B12, we then investigated whether it reduced the production of Aβ40 in a similar manner to 2B12. Aβ40 levels from MOG cells incubated with either media alone or media containing 10 µg/ml 2B12, 2B3, the anti-N-terminal APP antibody or the irrelevant mouse IgG for 2 days were measured. The results were expressed as a percentage of the media control which was taken as 100%. Similarly to our previous results (Thomas et al., 2006), we found that the irrelevant IgG reduced the production of Aβ40 by 10.5% which was not significant (FIG. 7). The anti-N-terminal APP antibody increased the production of Aβ40 by 6.8% which was also not significant (FIG. 7). 2B12 significantly inhibited the production of Aβ40 by MOG cells by 34.7% compared to control, a similar result to that we had obtained before (Thomas et al., 2006). However, 2B3 produced a much greater inhibition of Aβ40 production by MOG cells of 63.2% which was significantly different to both control and 2B12 (FIG. 7). These data clearly demonstrate that 2B3 can block the access of β-secretase to its cleavage site more effectively than 2B12 and thus produce a greater reduction in the production of Aβ40. It is likely that this is due to increased binding of 2B3 to APP shown above (FIG. 3). Furthermore, we have now demonstrated that neither incubation with a large protein (irrelevant IgG) nor with another antibody which binds to a different region of APP upstream of 2B3 and 2B12 (anti-N-terminal APP antibody), produces steric hindrance of the action of β-secretase. These data suggest that our findings are due to the specific effect of our antibodies on β-secretase activity.

Our data have shown that 2B3 is a significantly better antibody than 2B12 with regard to its binding to APP, its half-maximal binding to Kb and its ability to inhibit the production of Aβ40. In addition, 2B3 is different to the antibody produced by Arbel et al. (2005) as it is raised to the native peptide spanning the β-secretase cleavage site rather than to the half-Swedish mutation peptide used by Arbel and co-workers (2005). This is advantageous as the majority of people with AD do not express this mutation so our antibody will recognise the constitutively expressed APP found in the majority of AD patients very efficiently. In addition, unlike Arbel et al. (2005), 2B3 was characterised using a cell line which expresses endogenous APP, not one which over-expresses this protein. Again this reflects the situation seen in the majority of AD sufferers who do not express the very high levels of APP found in transfected cells. The very large decreases in Aβ40 seen in this system suggest that 2B3 might be effective in man while there is no comparable data available for the antibody made by Arbel et al. (2005).

REFERENCES

Alzheimer' Society website, www.alzheimers.org.uk
Arbel, M., Yacoby, I. and Solomon, B. (2005) PNAS 102 7718-7723
Chong, Y. H., Jung, J. M., Choi, W., Park, C. W., Choi K. S. and Suh, Y.-H. (1994) Life Sciences 54 1259-1268
Citron, M. (2004) Nat. Rev. Neurosci. 5 677-685
Dominguez, D., Tournoy, J., Hartmann, D., Huth, T., Cryns, K., Deforce, S., Serneels, L., Espuny Camacho, I., Marjaux, E., Craessaerts, K., Roebroek, A. J. M., Schwake, M., D'Hooge, R., Bach, P., Kalinke, U., Moechars, D., Alzheimer, C., Reiss, K., Saftig, P. and De Strooper, B. (2005) J. Biol. Chem. 280 30797-30806
Kidd, E. J., Miller, K. J., Sansum A. J. and Humphrey, P. P. A. (1998) Neurosci. 87 533-539
Kohler, G. and Milstein, C. (1975) Nature 256 495-497
Liddell, J. E. and Cryer, A. (1991) A Practical Guide to Monoclonal Antibodies, John Wiley & Sons Ltd, Chichester
Paganetti, P., Calcanca, V., Galli, C., Stefani, M, and Molinari, M. (2005) J. Cell Biol. 168 863-868
Rakover, I., Arbel, M. and Solomon, B. (2007) Neurodegen. Dis. 4 392-402 et al., 2007
Thomas, R. S., Liddell, J. E., Murphy, L. S., Pache, D. M. and Kidd, E. J. (2006) J. Alz. Dis. 10 379-390

The invention claimed is:

1. An amyloid precursor protein (APP)-binding monoclonal antibody 2B3-E10-A8-B10-F10-H3 (2B3), or an antigen-binding fragment thereof, wherein the monoclonal antibody or antigen-binding fragment thereof is capable of reducing the release or accumulation of β-amyloid when administered outside an APP-expressing cell.

2. The APP-binding monoclonal antibody or antigen-binding fragment thereof according to claim 1 wherein said monoclonal antibody or fragment binds to the whole or a part of the β-secretase cleavage site of APP (ISEVKMDA; SEQ ID NO 1).

3. The APP-binding monoclonal antibody or antigen-binding fragment thereof according to claim 1 wherein said monoclonal antibody is generated by immunization with the antigenic peptide EEISEVKMDAEFRHD (SEQ ID NO 3).

4. The APP-binding monoclonal antibody or antigen-binding fragment thereof according to claim 3 wherein said antigenic peptide is conjugated to a multi-antigenic peptide.

5. The APP-binding monoclonal antibody or antigen-binding fragment thereof according to claim 1 wherein the binding of the monoclonal antibody or fragment thereof to APP protein results in a reduction in β-amyloid such that there is a greater than 45% inhibition of β-amyloid release or accumulation.

6. The APP-binding monoclonal antibody or antigen-binding fragment thereof according to claim 1 wherein the half-maximal binding of the monoclonal antibody or fragment thereof to the APP protein is less than 2.96 ug/ml.

7. The APP-binding monoclonal antibody or antigen-binding fragment thereof according to claim 1 wherein the APP-expressing cell is a mammalian cell or a mammalian cell line.

8. The APP-binding monoclonal antibody or antigen-binding fragment thereof according to claim 7 wherein said cell or said cell line is a human cell or a human cell line.

9. A pharmaceutical composition comprising an effective amount of APP-binding monoclonal antibody or antigen-binding fragment thereof according to claim 1.

10. The pharmaceutical composition according to claim 9 wherein said, composition is formulated for intravenous, subcutaneous, intramuscular, intrathecal, nasal, inhalation, depot injection or implantation administration.

11. The pharmaceutical composition according to claim 10, comprising a pharmaceutically acceptable adjuvant, carrier or vehicle.

12. An isolated cell or cell line which secretes the APP binding monoclonal antibody or antigen-binding fragment thereof according to claim 1.

13. A vector comprising a nucleic acid molecule encoding the APP-binding monoclonal antibody or antigen-binding fragment thereof according to claim 1.

14. A method for the treatment of an individual suffering from, or suspected to be suffering from, Alzheimer's Disease or an aetiologically related disease that is characterised by the production of elevated levels of β-amyloid wherein an effective amount of monoclonal antibody or antigen-binding fragment thereof according to claim 1 is administered to said individual.

15. The method according to claim 14 wherein the monoclonal antibody or antigen-binding fragment thereof is administered outside an APP-expressing cell of said individual.

16. The method according to claim 15 wherein an effective amount of the monoclonal antibody or antigen-binding fragment thereof is administered or injected, intravenously, subcutaneously or intramuscularly or is administered into the cerebral spinal fluid or is administered or injected at a site to be treated or is administered nasally or via inhalation, or is administered by depot injection or implantation.

* * * * *

SEQUENCE LISTING

<160> NUMBER OF SEQ ID NOS: 4

<210> SEQ ID NO 1
<211> LENGTH: 8
<212> TYPE: PRT
<213> ORGANISM: Human

<400> SEQUENCE: 1

Ile Ser Glu Val Lys Met Asp Ala
1               5

<210> SEQ ID NO 2
<211> LENGTH: 8
<212> TYPE: PRT
<213> ORGANISM: Human

<400> SEQUENCE: 2

Ile Ser Glu Val Lys Leu Asp Ala
1               5

<210> SEQ ID NO 3
<211> LENGTH: 15
<212> TYPE: PRT
<213> ORGANISM: Human

<400> SEQUENCE: 3

Glu Glu Ile Ser Glu Val Lys Met Asp Ala Glu Phe Arg His Asp
1               5                   10                  15

<210> SEQ ID NO 4
<211> LENGTH: 15
<212> TYPE: PRT
<213> ORGANISM: Human

<400> SEQUENCE: 4

Ser Glu Val Lys Met Asp Ala Glu Phe Arg His Asp Ser Gly Tyr
1               5                   10                  15